US012575774B2

(12) United States Patent
Reed et al.

(10) Patent No.: US 12,575,774 B2
(45) Date of Patent: Mar. 17, 2026

(54) HYDROGEL PAD

(71) Applicant: Welch Allyn, Inc., Skaneateles Falls, NY (US)

(72) Inventors: Shelby Michael Reed, Phoenix, NY (US); Carlos Suarez, Syracuse, NY (US); Thaddeus Wawro, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1192 days.

(21) Appl. No.: 17/240,431

(22) Filed: Apr. 26, 2021

(65) Prior Publication Data

US 2021/0353198 A1      Nov. 18, 2021

Related U.S. Application Data

(60) Provisional application No. 63/023,988, filed on May 13, 2020.

(51) Int. Cl.
A61B 5/259      (2021.01)
A61B 5/05      (2021.01)

(52) U.S. Cl.
CPC ................................... A61B 5/259 (2021.01)

(58) Field of Classification Search
CPC ....... A61B 5/259; A61B 5/282; A61B 5/6833; A61B 5/291; A61B 5/0006; A61B 5/257; A61B 2562/0217; A61B 2560/0412; A61B 5/28; A61B 2562/125; A61B 5/6814; A61B 5/266; A61B 5/6804

USPC .......................................... 600/372, 382–393
See application file for complete search history.

(56) References Cited

U.S. PATENT DOCUMENTS

| | | | | |
|---|---|---|---|---|
| 6,301,493 | B1 * | 10/2001 | Marro | ................. A61B 5/6803 |
| | | | | 600/383 |
| 8,337,389 | B2 | 12/2012 | Dlugos, Jr. et al. | |
| 2005/0015134 | A1 * | 1/2005 | Carim | .................... A61B 5/257 |
| | | | | 607/142 |
| 2008/0281178 | A1 * | 11/2008 | Chuang | ................ A61B 5/6833 |
| | | | | 600/347 |
| 2013/0079618 | A1 * | 3/2013 | Sandmore | .............. A61B 5/291 |
| | | | | 29/402.08 |
| 2015/0148646 | A1 * | 5/2015 | Park | ....................... A61B 5/259 |
| | | | | 174/262 |

(Continued)

FOREIGN PATENT DOCUMENTS

WO            2020039431 A1      2/2020

*Primary Examiner* — Joseph A Stoklosa
*Assistant Examiner* — Brian M Antiskay
(74) *Attorney, Agent, or Firm* — Merchant & Gould P.C.

(57) ABSTRACT

A hydrogel pad is configured for use with an electrode or a wearable device to measure vital signs of a patient. The hydrogel pad includes a flexible support having one or more openings in which hydrogel is disposed. A membrane covers one side of the hydrogel to protect it from gaining or losing too much moisture. A removable backing covers the other side of the hydrogel until it is applied to a patient, at which point the other side contacts the patient's skin. The protective membrane can be pierced by an angular conductive contact of a device to contact the hydrogel creating an electric conduit between the patient and the device. When the device is removed, the membrane at least partially closes to cover and protect the hydrogel.

4 Claims, 7 Drawing Sheets

(56)          References Cited

U.S. PATENT DOCUMENTS

| | | |
|---|---|---|
| 2019/0239976 A1 | 8/2019 | Mcclellan |
| 2019/0344069 A1 | 11/2019 | Maesani et al. |

* cited by examiner

HYDROGEL PAD

BACKGROUND

An electrode is used to couple electrical signals from the body into an electronic device, such as a wearable patch. The electrical signals can be used by the device to measure impedance and determine a variety of vital signs, such as electrical activity of the heart (ECG/EKG) or neuronal activity of the brain (EEG). Electrodes are typically coupled to a hydrogel that provides an electrically conductive path between the device and the wearer's skin. In order to operate properly, the hydrogel must maintain a particular amount of water. Exposure to air can dry out the hydrogel, while exposure to too much moisture can oversaturate the hydrogel. Such conditions can impact the ability for the hydrogel to function as the desired conductive path.

SUMMARY

Embodiments of the disclosure are directed to hydrogel pads. More specifically, the hydrogel pads have membranes that protect the hydrogel so that the hydrogel pad can remain on a patient even after an electronic device is removed.

In one aspect, a hydrogel pad includes a flexible support having a first surface, a second surface opposite the first surface, and a first opening through a thickness of the flexible support; a first hydrogel portion disposed within the first opening, the first hydrogel portion having a first surface adjacent the first surface of the flexible support and a second surface adjacent the second surface of the flexible support; and a membrane covering the second surface of the first hydrogel portion and affixed to the second surface of the flexible support.

In another aspect, a vital signs monitoring device includes a hydrogel pad and a vitals sign patch device. The hydrogel pad has a first side configured to contact skin of a patient, and a second side opposite the first side and configured to contact conductive contacts of a vital signs patch device. The hydrogel pad includes a flexible support having a first opening and a second opening; a first hydrogel portion disposed within the first opening and a second hydrogel portion disposed within the second opening; and a thin protective membrane covering each of the first hydrogel portion and the second hydrogel portion on the first side of the hydrogel pad, the thin protective membrane having a perforation positioned over each hydrogel portion, wherein the thin protective membrane is affixed to the flexible support. The vital signs patch device includes a housing containing a processing device and a memory device; and a first conductive contact and a second conductive contact in electrical communication with the processing device, the first conductive contact and the second conductive contact each protruding from the housing and having a pointed shape, wherein the first conductive contact is configured to pierce the perforation in the thin protective membrane over the first hydrogel portion and contact the first hydrogel portion, and the second conductive contact is configured to pierce the perforation in the thin protective membrane over the second hydrogel portion and contact the second hydrogel portion.

In yet another aspect, an electrode assembly includes a hydrogel pad and an electrode contact. The hydrogel pad has a first side configured to contact skin of a patient, and a second side opposite the first side and configured to contact an electrode, the hydrogel pad comprising: a flexible support having an essentially flat shape with a first surface, a second surface opposite the first surface, and an opening through a thickness of the flexible support; a hydrogel portion disposed within the opening, the hydrogel portion having a first surface adjacent the first surface of the flexible support and a second surface adjacent the second surface of the flexible support, the hydrogel portion having a thickness essentially equal to the thickness of the flexible support; and a thin protective membrane covering the second surface of the hydrogel portion and adhered to the second surface of the flexible support. The electrode contact includes a support surface comprising non-conductive material; a piercing contact comprising conductive material shaped to puncture through the membrane and contact the first hydrogel portion; and a conductive lead wire coupled to the piercing contact and configured to electrically couple the electrode contact to a device.

The details of one or more techniques are set forth in the accompanying drawings and the description below. Other features, objects, and advantages of these techniques will be apparent from the description, drawings, and claims.

DETAILED DESCRIPTION

Figure 1:
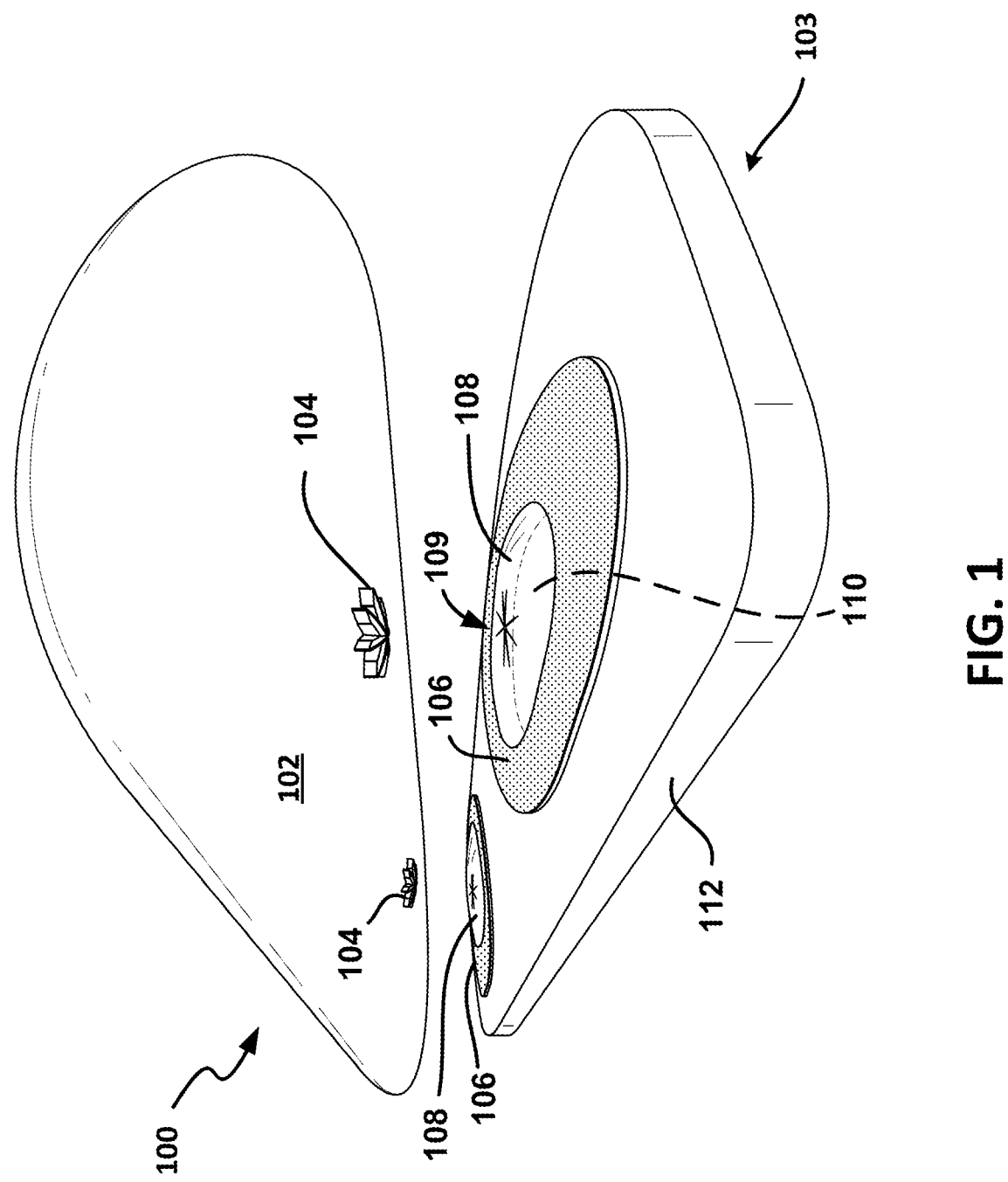
FIG. 1 illustrates a perspective view of a vital signs patch device positioned above a hydrogel pad.

The present disclosure is directed to a hydrogel pad. In some embodiments, the hydrogel pad is utilized with an electrode or a wearable device to measure vital signs of a patient. The hydrogel pad operates to provide a conductive path between the patient's skin and the device. The electrical resistance of the hydrogel can change based on the water content of the hydrogel. When the hydrogel's resistance changes, it can affect the measurements taken with the electrode or device. For that reason, the hydrogel pad is protected by a support structure that surrounds a perimeter of the hydrogel. Additionally, a protective membrane covers one side of the pad and a removable backing covers the other side until the hydrogel pad is placed on the patient.

In some embodiments, the protective membrane includes a perforation that can be pierced by a conductive contact of the electrode or device. The perforation is shaped to allow openings in the membrane to expand when the conductive contacts pass through and then retract back to protect the membrane when the piercing contacts are removed. In alternative embodiments, the protective membrane is made from self-healing materials that will close around punctures made by piercing contacts after a device is removed. This allows the electrode or device to be removed from the patient temporarily and then replaced without removing or replacing the hydrogel pad.

This is beneficial for various applications, such as performing an MM, bathing the patient, or replacing a device that needs to be recharged. Removing the sticky hydrogel from the patient's skin can be uncomfortable, so it is preferred to avoid removing a hydrogel if it is going to be replaced immediately.

Various types of devices can be utilized with the hydrogel pads described herein. Such devices include wearable vital sign monitoring patches, electrode assemblies, and other wearable devices. In some embodiments, the device includes one body or housing having two conductive piercing contacts and those contacts pierce into hydrogel on two separate hydrogel pads. In some embodiments, the device is a single electrode having one conductive piercing contact and one single hydrogel pad. Unless otherwise specified, the term "device" is intended to mean any type of device that is coupled to a hydrogel pad to receive electrical impulses from a patient's body.

The term "patient" as used herein is intended to mean any species of animal. In some embodiments, the patient is a mammal. In some embodiments, the patient is a human being. FIGS. 1-4 illustrate an example device assembly 100 for monitoring vital signs.

Generally, the device assembly 100 includes a vital signs patch device 102 and a hydrogel pad 103. The vital signs patch device 102 operates to record vital signs data received through electrical signals received from a patient's body through the conductive hydrogel pad 103. Note that this is merely one illustrative example. Many other configurations of devices and hydrogel pads are contemplated within the scope of this disclosure.

Figure 2:
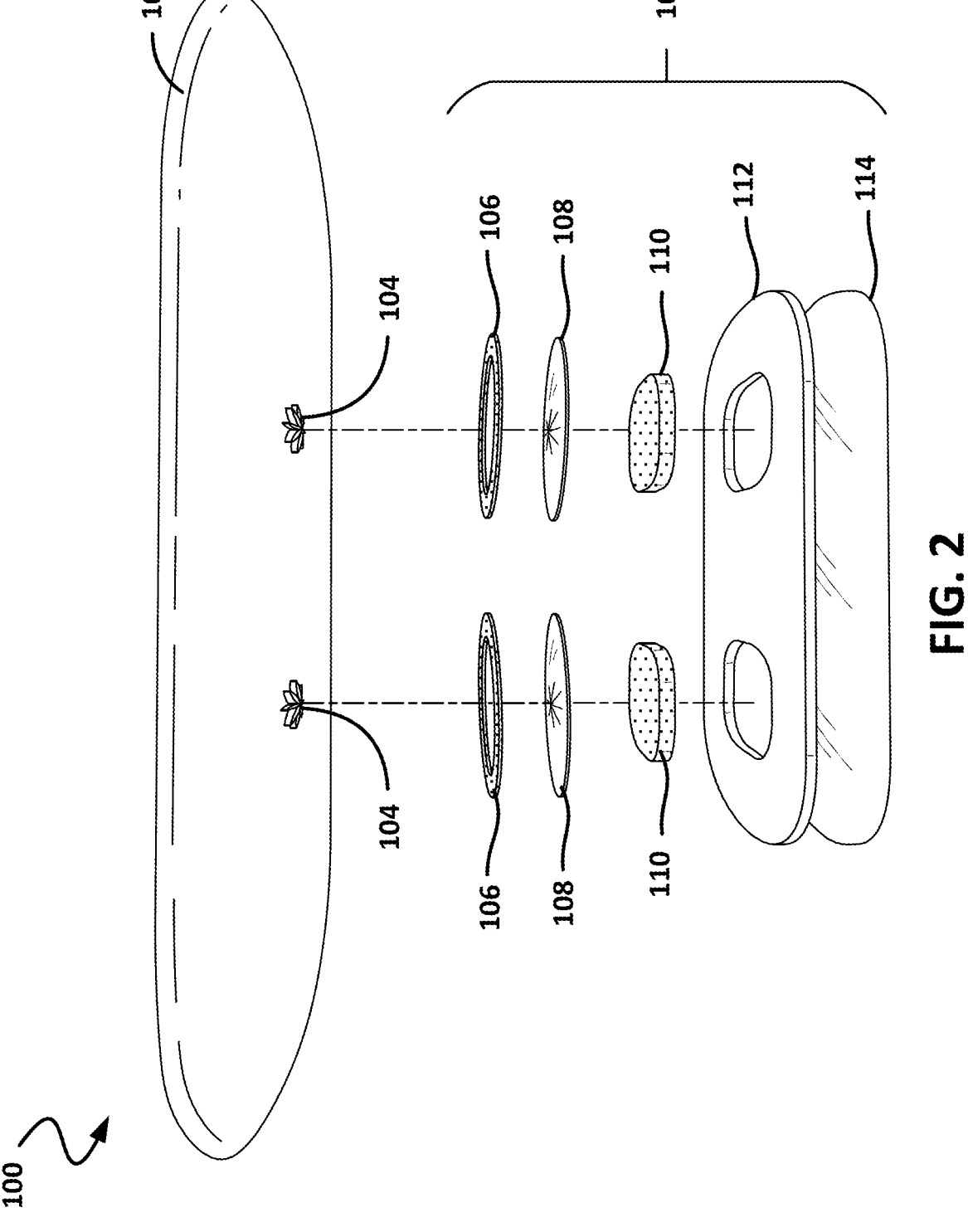
FIG. 2 illustrates an exploded side view of a device assembly including the vital signs patch device and hydrogel pad of FIG. 1.
Figure 3:
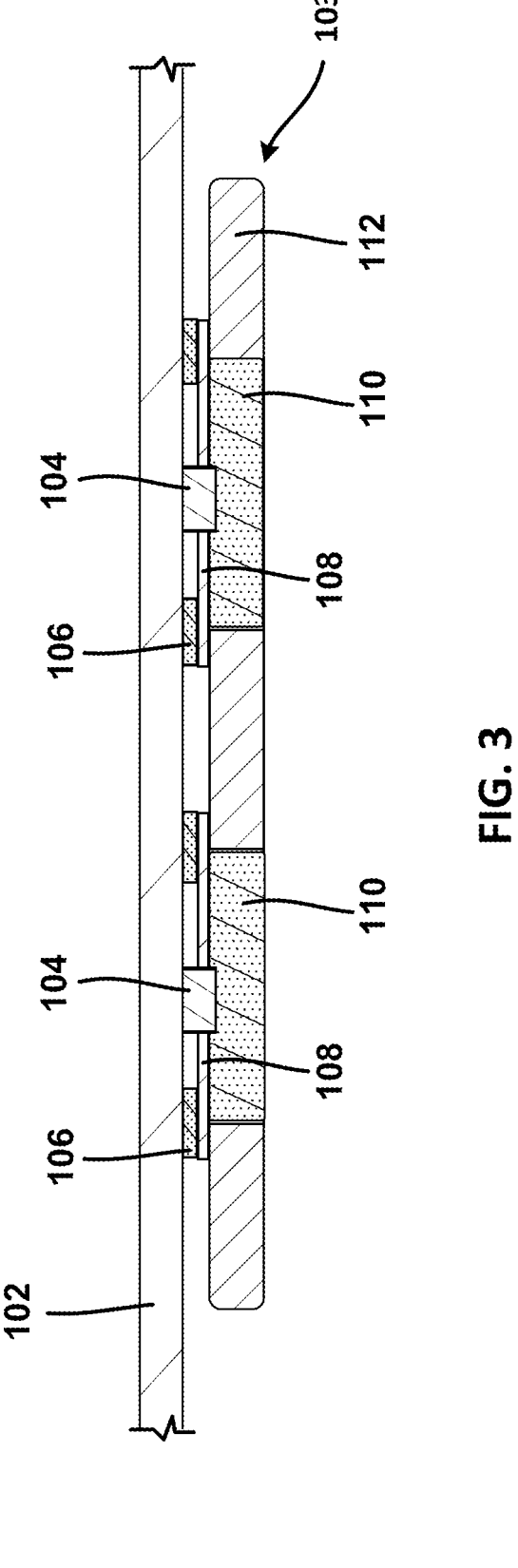
FIG. 3 illustrates a cutaway side view of the device assembly with the vital signs patch device joined to the hydrogel pad.
Figure 4:
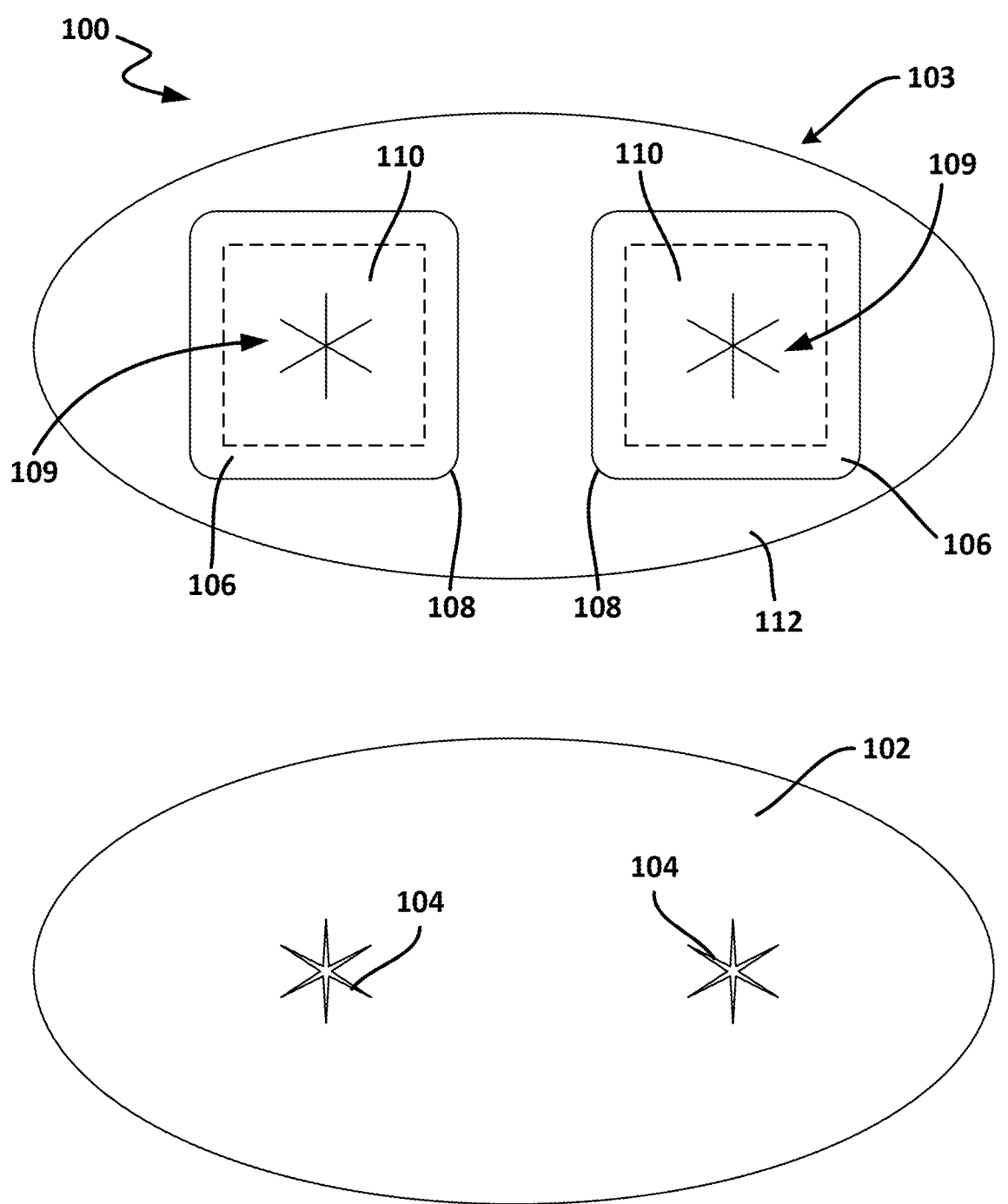
FIG. 4 shows a top view of the hydrogel pad next to a bottom view of the vital signs patch device.

FIG. 1 illustrates a perspective view of the vital signs patch device 102 positioned above the hydrogel pad 103. FIG. 2 illustrates an exploded side view of the device assembly 100. FIG. 3 illustrates a cutaway side view of the device assembly 100 when the vital signs patch device 102 is joined to the hydrogel pad 103. FIG. 4 shows a top view of the hydrogel pad 103 next to a bottom view of the vital signs patch device 102. The following description refers generally to FIGS. 1-4, unless otherwise specified.

The vital signs patch device 102 includes two piercing contacts 104. The piercing contacts 104 are made of conductive material that provide a conduit between the conductive hydrogel pad 103 and the circuitry of the vital signs patch device 102. In this example, the piercing contacts 104 have a starburst design configured to pierce through a perforation 109 in the protective membrane 108 covering the hydrogel 110. The top view in FIG. 4 shows how the perforations 109 in the membrane 108 are congruent with the shape of the piercing contacts 104. The perforations 109 are spaced on the hydrogel pad 103 to line up with the piercing contacts 104 that are spaced on the vital signs patch device 102. As the piercing contact 104 presses against the slits in the perforation 109, it displaces the membrane 108 and comes in contact with the hydrogel 110. Then as the piercing contact 104 is removed, the membrane 108 returns to its original configuration and the slits are rejoined to cover the hydrogel 110.

In some embodiments, the piercing contacts 104 have other angular shapes to facilitate piercing a membrane such as a cross or plus shape, a five sided star, a pyramid, or a conical point. The piercing contacts 104 are shaped for optimal surface area contact with the hydrogel 110 while also being capable of piercing through the membrane 108. While the example shown in FIGS. 1-4 has two piercing contacts 104, other examples could have one or three or four or five. If there is only one piercing contact 104 on an electrode, for example, the corresponding hydrogel 110 will have one membrane 108 with one perforation to align with the piercing contact 104.

In some embodiments, the piercing contacts 104 are made of conductive material such as metal (e.g., steel, aluminum, silver, gold). In some embodiments, the piercing contacts 104 are made of conductive polymers such as carbon black polymer composites, highly conductive poly(methyl methacrylate) (PMMA)-reduced graphene oxide composite or conductive polystyrene (PS). In some embodiments, the piercing contacts are made of a combination of plastic and carbon or polymers coated with metals. In some embodiments, the piercing contacts 104 are made with silver/silver chloride.

The hydrogel pad 103 operates to conduct electrical signals from a patient's body to the vital signs patch device 102 or any other attached device or electrode. The hydrogel pad 103 includes a hydrogel 110 as well as additional components to protect the hydrogel 110 from becoming oversaturated or under-saturated with water. The hydrogel pad 103 includes a flexible support 112, a protective membrane 108, and a hydrogel 110.

The hydrogel 110 operates to provide the electrically conductive medium through which electrical signals pass between a patient's body and a device. The hydrogel 110 is a tacky viscoelastic solid having greater cohesive strength than adhesive strength, ensuring that the material can be removed from a patient without breaking away from the support.

The size and shape of the hydrogel 110 can vary for aesthetic or practical purposes. Generally, the hydrogel 110 is a thin, flat layer of material having two opposite surfaces, a thickness, and a perimeter. In some embodiments, the hydrogel 110 has a rounded shape such as a rounded rectangle, a rounded square, an oval, or a circle. In some embodiments, the hydrogel 110 has a shape with corners such as a rectangle or square. The size of the hydrogel 110 can range from 0.2 to 10 mm in thickness with a surface area of from 1 to 30 square centimeters.

In some embodiments, the hydrogel 110 is a homogeneous aqueous mixture of water, an electrolyte, and a cross-linked polyethylene oxide (PEO). Any water soluble tacky polymer or co-polymer or blend of polymers which are radiation crosslinkable are capable of forming a cross-linked adhesive hydrogel sheet. Among others, polyvinyl alcohol or polyacrylamide may be utilized in the same way as the polyethylene oxide to yield an adhesive crosslinked hydrogel electrode. Blends as with polyethylene oxide and other polymers or co-polymers may accomplish the same.

To contribute to the strength of the hydrogel, both in tension and flexure, a low area-weight scrim can be incorporated into the film during fabrication before crosslinking. The scrim is preferably fabricated from a natural or synthetic hydrophobic polymer, e.g., a polyethylene, polypropylene, polyester, or polyamide homopolymer.

The flexible support 112 provides protection around the hydrogel 110 as well as structure for other components to interact with. In this example, the flexible support 112 is made of foam and surrounds the perimeter of each hydrogel 110. The flexible support 112 also serves to provide separation between the two hydrogels 110. The flexible support 112 has an essentially flat shape with a thickness similar to or equal to the thickness of the hydrogel 110. A perimeter of the flexible support 112 can have a similar shape to the perimeter of the hydrogel 110. In some embodiments, the perimeter of the flexible support 112 has a different shape from the perimeter of the hydrogel 110. A minimum amount of material is required to be present around the hydrogel 110 to properly protect it from changes in moisture content. In some embodiments, there is at least 5 millimeters of material surrounding each hydrogel 110.

The flexible support 112 has two sides. A first side is configured to contact a patient's skin. In some embodiments, the first side has adhesive on it that would be covered by a backing until the hydrogel pad 103 is applied to the patient. The first side is opposite the second side. The second side is configured to interface with the vital sign patch device 102. In some embodiments, the second side does not have adhesive. In some embodiments, the second side has adhesive 106 that contacts the vital sign patch device 102 to secure it in place. In some embodiments, the adhesive is a pressure sensitive adhesive.

The flexible support 112 is made of non-conductive, electrically insulating material. In some embodiments, the flexible support 112 is made of a polyurethane foam. In some embodiments, the flexible support 112 is made of other flexible polymers. Other suitable materials include polyethylene foam, fabric, polyolefin, polyester, and vinyl.

The protective membrane 108 operates to cover the hydrogels 110 to protect them from contact with moisture or air. The membrane 108 is positioned over the hydrogel 110 and is attached to the flexible support 112. When pressure is applied from the piercing contacts 104, the membrane 108 separates and allows only the contacts to penetrate the hydrogel 110. When the piercing contacts 104 are removed, the membrane closes to its original position, preventing air and water from ingressing to compromise the hydrogel. The membrane 108 is made of non-conductive, flexible, polymer-based material.

In some embodiments, the membrane 108 includes a perforation 109 over each hydrogel 110. The perforation 109 allows the piercing contacts 104 to pass through to the hydrogel 110 when the vital signs patch device 102 is attached to the hydrogel pad 103. The perforation could have a cross shape, a star shape, an asterisk shape, a hole, or a slit. In some embodiments, the perforation is a slit in the membrane that opens when a device is applied and seals when the device is removed, similar to a one-way valve. In some embodiments, the perforation comprises two or more intersecting slits that create multiple pointed flaps of membrane material that press into the hydrogel when the piercing contacts 104 are pressed against the membrane, creating an opening in the membrane 108. When the piercing contacts 104 are removed, the pointed flaps flex back to their original positions, covering the hydrogel. This configuration would operate much like pressing a straw through a slotted opening in a plastic lid of a beverage.

In some embodiments, the membrane 108 is a self-healing membrane that can allow the piercing contact 104 to pass through and then close again when the piercing contact 104 is removed. In some embodiments, the membrane 108 is capable of completely resealing. In some embodiments, the membrane 108 can partially close the holes left from being punctured. In some embodiments, the membrane 108 is made of a self-healing elastomeric material such as silicone.

The adhesive 106 operates to hold components of the hydrogel pad 103 together. For example, adhesive 106 is used to affix the membrane 108 to the flexible support 112. The adhesive 106 further operates to prevent fluid ingress to the hydrogel pad 103. In some embodiments, the adhesive 106 is silicone elastomer glue. In some embodiments, the adhesive 106 is a pressure-sensitive adhesive used to temporary hold components of the hydrogel pad 103 and a corresponding device together.

A label or removable backing 114 operates to cover the bottom side of the hydrogel and cover any adhesive on the bottom side of the flexible support 112 until the hydrogel pad 103 is applied to a patient. The removable backing 114 is releasably attached to the hydrogel pad 103 for easy removal. The removable backing 114 protects the hydrogel from drying out or coming into contact with too much moisture while it is in storage. Additionally the removable backing 114 prevents the hydrogel pad 103 from sticking to other objects before it is placed on a patient.

In some embodiments, the removable backing 114 comprises a hydrophobic sheet made of polyethylene or plastic coated release paper.

Figure 5B:
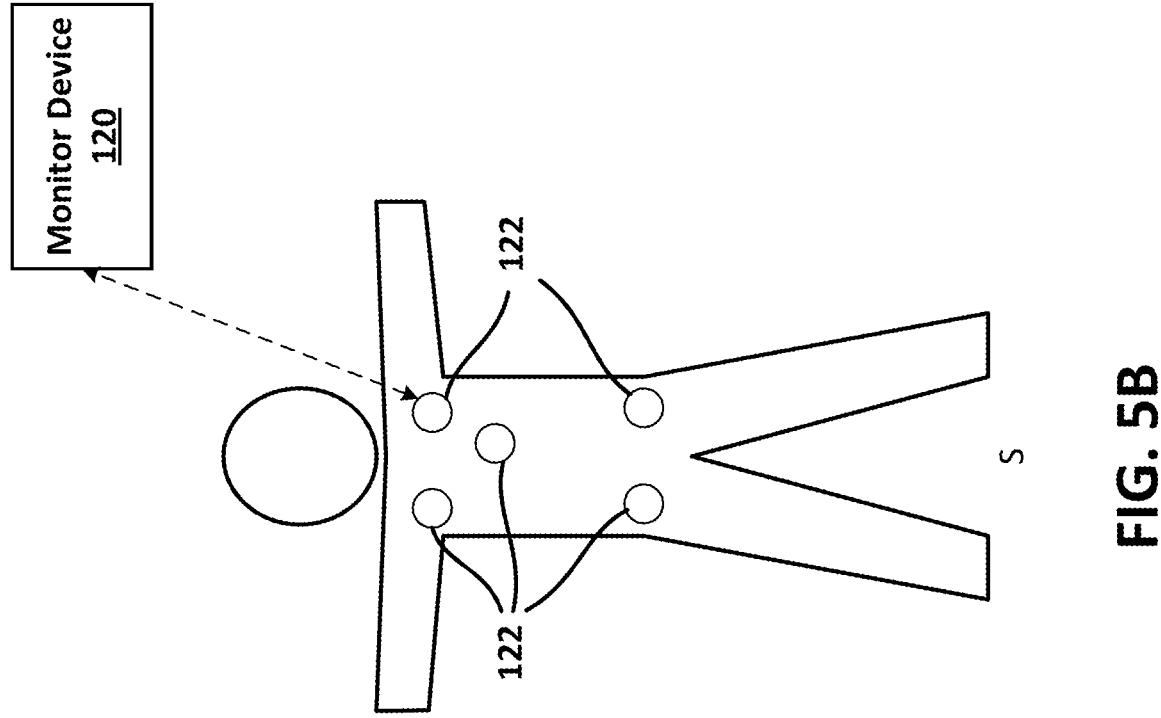
FIG. 5B illustrates an example of multiple electrode assemblies applied to a subject.
Figure 5A:
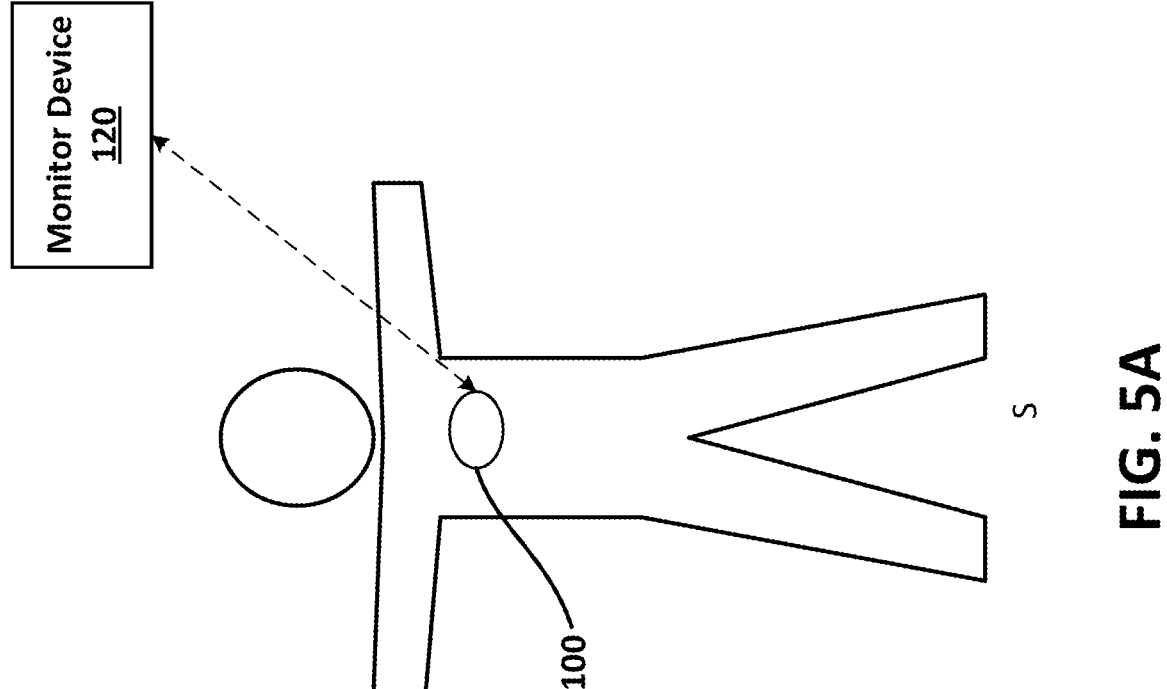
FIG. 5A illustrates an example device assembly applied to a subject.

FIGS. 5A and 5B illustrate two applications of hydrogel pads. In 5A, an example device assembly 100 is applied to the chest of a subject S. The device assembly 100 includes a vital signs patch device 102 and a hydrogel pad 103 as shown in FIGS. 1-4. Hydrogel pad 103 configurations such as those shown in FIGS. 1-4 and the example hydrogel pads 126 and 136 of FIGS. 6A and 6F would be appropriate for this particular use because they include two hydrogel 110 portions to receive two piercing contacts 104.

The vital signs patch device 102 operates to record vital signs data such as heart rate, blood pressure, and pulse oximetry. In some embodiments, the vital signs patch device 102 records an electrocardiogram (ECG/EKG). The vital signs patch device 102 is in communication with a monitor device 120 that operates to receive vital signs data, store the vital signs data, and communicate the vital signs data to other systems. One example of a monitor device 120 is the Connex® Spot Monitor (Welch Allyn®, Skaneateles Falls, N.Y.).

In some embodiments, the vital signs patch device 102 includes a processor, a memory device, and a portable power source (e.g. rechargeable battery). The memory device includes instructions that, when executed by the processor, cause the vital signs patch device 102 to monitor a patient's vital signs and communicate vital signs data to the monitor device 120. In some embodiments, the vital signs patch device 102 is a wearable device that communicates with the monitor device wirelessly.

In some embodiments, the vital signs patch device 102 does not include a processor, a memory device, and a portable power source. Instead, power is received from an electrical cable connected to a power outlet. Additionally, the vital signs patch device 102 is in wired connection with the monitor device 120. The monitor device 120 includes a processor and memory including instructions to operate the vital signs patch device 102. Data from the vital signs patch device 102 is communicated directly to the monitor device 120.

In 5B, multiple electrode assemblies 122 are applied to the body of the subject S. Each electrode assembly 122 includes a hydrogel pad 103 and an attached electrode contact. The electrode contact is generally attached to another device, such as the monitoring device 120, via lead wires. Appropriate hydrogel pad arrangements include example hydrogel pads 128, 130, 132, and 134 shown in FIGS. 6B-6E. In the example of 5B, five electrode assemblies 122 are shown. However, other configurations and numbers of electrode assemblies 122 are possible. The electrode assemblies 122 can operate with the monitoring device 120 as described above in FIG. 5A.

FIGS. 6A-6F illustrate alternative embodiments of hydrogel pads 103. Many different shapes and sizes of hydrogel 110 portions can be utilized with different shapes and sizes of flexible supports 112. In some embodiments, there are two hydrogel 110 portions within each flexible support 112. These types of hydrogel pads 103 might be used with a device having two electrical contacts. In some embodiments, there is one hydrogel 110 portion within each flexible support 112. This type of hydrogel pad 103 might be used with a more traditional electrode assembly and more than one electrode assembly would be used at a time on a patient (e.g., as shown in FIG. 5B).

Figures 6A, 6B, 6C:
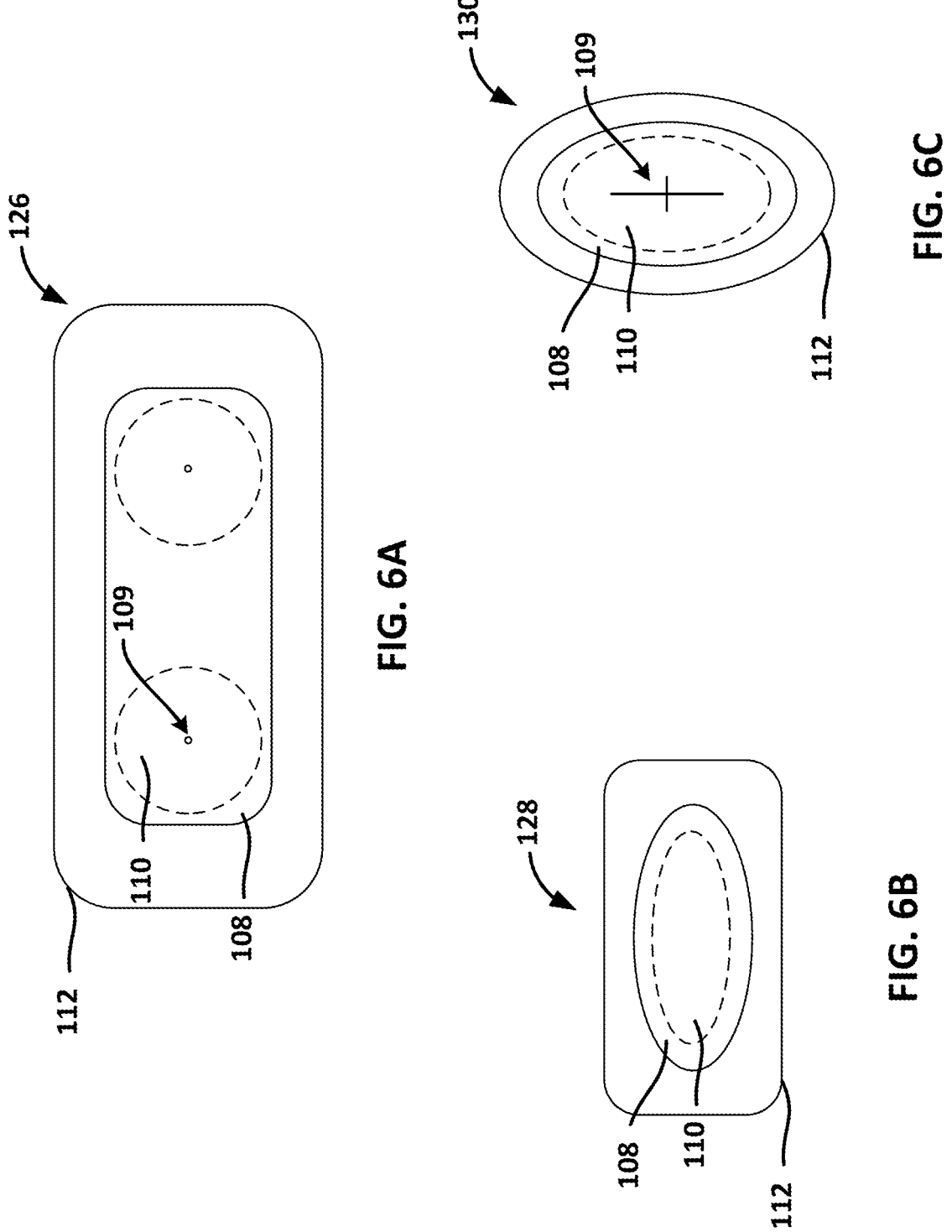
FIGS. 6A-6F illustrate various examples of hydrogel pads.

FIG. 6A illustrates a first example hydrogel pad 126 having two hydrogel 110 portions. In this example, the two hydrogel 110 portions are circular, the flexible support 112 has a rounded rectangular shape, and the membrane 108 also has a rounded rectangular shape that covers both hydrogels 110. The perforation 109 is a small hole in each hydrogel 110. In this example, the perforation 109 could stretch to accommodate a piercing contact and then retract again when the contact is removed. In some embodiments, the hydrogel pad 126 has overall dimensions of about 10 to 16 centimeters in length, about 4 to 8 centimeters in width, and about 1 to 10 millimeters in thickness.

FIG. 6B illustrates another example hydrogel pad 128 having a flexible support 112 having a rounded rectangular shape with a single elliptical hydrogel 110 and membrane 108. In this example, the membrane 108 does not include a perforation and is made of self-healing material. Attaching a device to the hydrogel pad 128 will pierce the membrane 108 with a sharp contact and then when the device is removed the membrane will close to at least partially reseal the hole. In some embodiments, the hydrogel pad 128 has overall dimensions of about 4 to 8 centimeters in length, about 2 to 4 centimeters in width, and about 1 to 10 millimeters in thickness.

In another example shown in FIG. 6C, the hydrogel pad 130 has a flexible support 112, hydrogel 110, and membrane 108 all having the same elliptical shape, but with slightly different sizes. The membrane 108 has a cross-shaped perforation made of two intersecting slits. In some embodiments, the hydrogel pad 130 has overall dimensions of about 4 to 8 centimeters in length, about 2 to 4 centimeters in width, and about 1 to 10 millimeters in thickness.

Figures 6D, 6E, 6F:
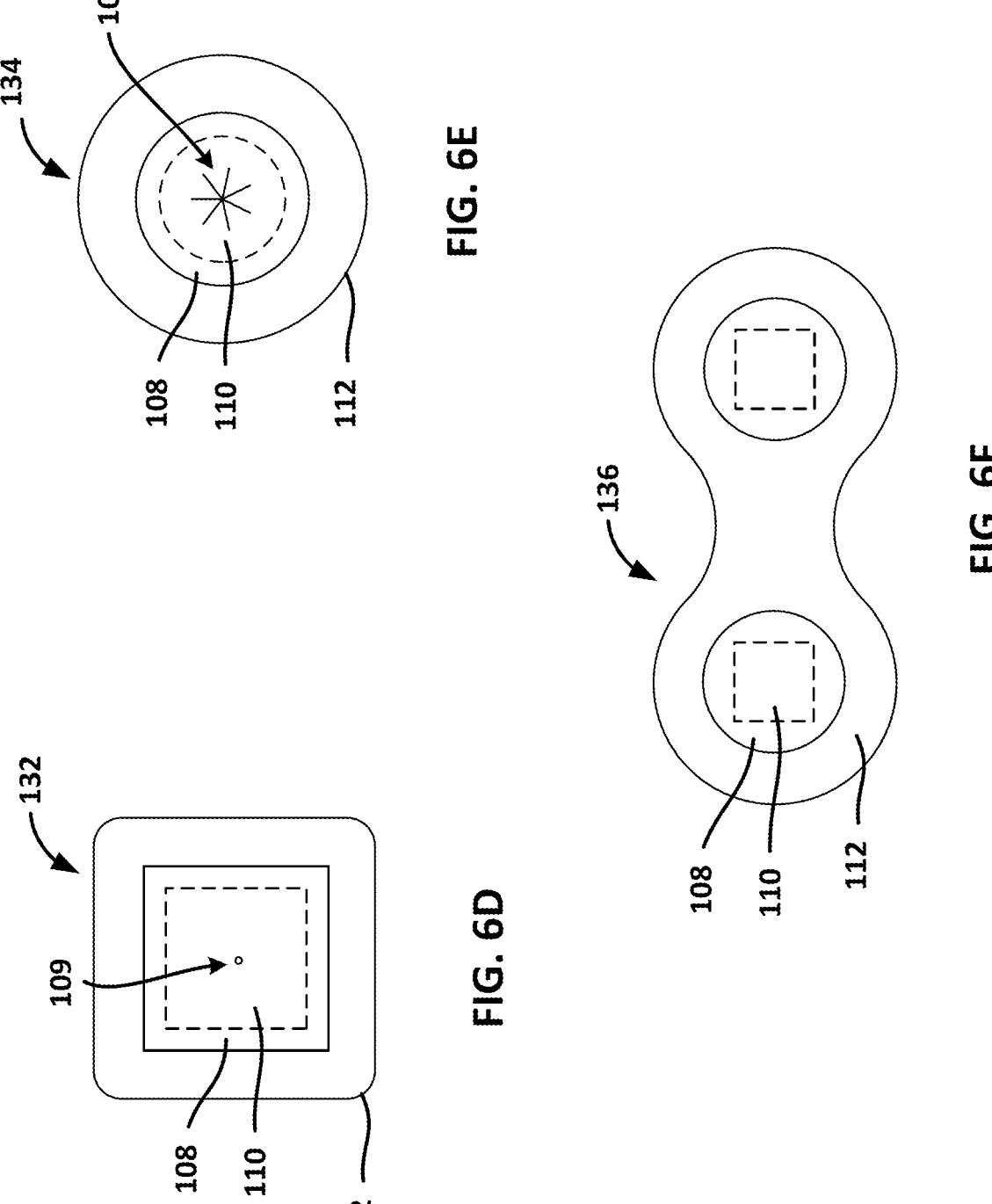

FIG. 6D illustrates another example hydrogel pad 132 having a rounded square flexible support 112 with a square hydrogel 110 and a square membrane 108. The membrane 108 includes a small hole perforation 109. In some embodiments, the hydrogel pad 132 has overall dimensions of about 3 to 9 centimeters in length, about 3 to 9 centimeters in width, and about 1 to 10 millimeters in thickness.

In another example shown in FIG. 6E, the hydrogel pad 134 has a round flexible support 112, a round hydrogel 110 and a round membrane 108. The membrane 108 includes a large star-shaped perforation with 8 arms intersecting at the center of the hydrogel 110. The longer slits allow for more flexibility in where the contacts are pressed through the membrane 108. In some embodiments, hydrogel pad 134 has a diameter of about 3 to 9 centimeters and a thickness of about 1 to 10 millimeters.

FIG. 6F illustrates a hydrogel pad 136 example with one flexible support 112 and two hydrogel 110 portions. The flexible support 112 has an oblong shape with two semi-round areas joined by a narrower connection. Each semi-round area has a square opening holding a square hydrogel 110 portion. Round membranes 108 cover each hydrogel 110. This hydrogel pad 136 might be used with a device having two contacts such as the vital signs patch device 102. In some embodiments, the hydrogel pad 136 has overall dimensions of about 10 to 16 centimeters in length, about 4 to 8 centimeters in width, and about 1 to 10 millimeters in thickness.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A hydrogel pad comprising:
   a flexible support having a first surface, a second surface opposite the first surface, and a first opening through a thickness of the flexible support;
   a first hydrogel portion disposed within the first opening, the first hydrogel portion having a first surface adjacent the first surface of the flexible support and a second surface adjacent the second surface of the flexible support;
   a membrane comprising non-conductive, flexible, polymer-based material covering the second surface of the first hydrogel portion and affixed to the second surface of the flexible support, wherein the membrane includes a perforation comprising one or more slits configured to allow a piercing contact of a device to pass through the membrane to the first hydrogel portion, establish electrical communication with the first hydrogel portion, and cover the first hydrogel portion after the piercing contact is removed, wherein the perforation is pre-formed and centrally positioned above the first hydrogel portion for alignment with the piercing contact of the device; and
   an adhesive positioned around the first hydrogel portion, the adhesive affixing the membrane to the flexible support, and the adhesive being configured to releasably affix the hydrogel pad to the device.

2. The hydrogel pad of claim 1, wherein the flexible support further comprises a second opening, a second hydrogel portion is disposed within the second opening, and the membrane is covering the second hydrogel portion.

3. The hydrogel pad of claim 1, wherein the membrane is a self-healing membrane configured to allow the piercing contact of the device to pass through to the first hydrogel portion and establish electrical communication while keeping moisture from passing through the membrane, and wherein the membrane closes after the piercing contact is removed.

4. The hydrogel pad of claim 1, further comprising a backing layer releasably affixed to the first surface of the first hydrogel portion and the first surface of the flexible support.

* * * * *